United States Patent [19]

Matson

[11] 4,201,646

[45] May 6, 1980

[54] APPARATUS FOR STRIPPING VOLTAMMETRY

[75] Inventor: Wayne R. Matson, Ayer, Mass.

[73] Assignee: Environmental Sciences Associates, Inc., Bedford, Mass.

[21] Appl. No.: 856,086

[22] Filed: Nov. 30, 1977

Related U.S. Application Data

[63] Continuation of Ser. No. 643,295, Dec. 22, 1975, abandoned, which is a continuation of Ser. No. 447,376, Mar. 1, 1974, abandoned.

[51] Int. Cl.$^2$ ............................................. G01N 27/48
[52] U.S. Cl. ........................... 204/195 H; 204/195 R; 204/195 T
[58] Field of Search ............... 204/1 T, 195 R, 195 H, 204/195 T, 222

[56] References Cited

U.S. PATENT DOCUMENTS

| | | | |
|---|---|---|---|
| 2,621,671 | 12/1952 | Eckfeldt | 204/195 T |
| 3,214,354 | 10/1965 | Capuano et al. | 204/195 R |
| 3,449,233 | 6/1969 | Morrow | 204/195 R |
| 3,859,193 | 1/1975 | Bednarski et al. | 204/195 H |

*Primary Examiner*—G. L. Kaplan
*Attorney, Agent, or Firm*—Strimbeck & Soloway

[57] ABSTRACT

A system is disclosed for voltammetry such as anodic stripping voltammetry including a special electrode mounted to be fitted into a sample holder, stirring means operable through the electrode and an electrolytic potential source, optionally pulsed, capable of scanning the operating potential range which may for example, be a range between about -1 volt and 0 volt. Output recording means can be either an analog chart output or digitalized output. The system may be employed for a wide variety of test purposes generally relating to identifying and measuring heavy metals, one of which is detecting and measuring trace mineral components or trace elements in samples of human blood. When employed with blood samples the sample may first be prepared in the usual manner including digesting the sample but the presently preferred procedure contemplates that the metals being tested are first displaced from blood complexing with suitable ion such as $Cr^{3+}$ or $Ca^{2+}$ and the operating potential from about -800 millivolts to nearly 0 volt is scanned to read out the presence and quantity of metal such as lead, cadmium, copper and the like. An analysis of such metals can be run in as little as a minute. The ratio of electrode area to sample volume disclosed is 4cm$^2$ per 1.0 milliliter. A self contained test composition is disclosed.

18 Claims, 5 Drawing Figures

APPARATUS FOR STRIPPING VOLTAMMETRY

CROSS-REFERENCES TO RELATED APPLICATIONS

This application is a continuation of an application Ser. No. 643,295 filed Dec. 22, 1975 (now abandoned), which in turn is a continuation of an application Ser. No. 447,376 filed Mar. 1, 1974 (now abandoned).

Other related applications include Wayne R. Matson's TESTING PRODUCT, Ser. No. 666,664 filed Mar. 15, 1976, now U.S. Pat. No. 4,090,926, issued May 23, 1978, which was a continuation of an application Ser. No. 505,149 filed Sept. 11, 1974 (now abandoned).

BACKGROUND OF THE INVENTION

It has long been possible to test both qualitatively and quantitatively for ionic materials in an aqueous sample by electrolytic means, and to record the electrical potential of deposition of the ions on an electrode. In one form of such testing known as stripping voltammetry, the ions are first deposited on an electrode and thereafter the potential is continuously or continually varied to strip the deposited material from the electrode and redissolve it in the sample liquid. This operation is known as stripping voltammetry and since it is ordinarily used by plating cathodically and stripping anodically to detect and measure metallic ions, it is often known as anodic stripping voltammetry. By means of anodic stripping voltammetry, it has been found possible to perform relatively quick simple and accurate tests to measure minute traces of appropriate materials. Recently, in connection with environmental studies, it has become important to collect small quantities of polluting impurities from the atmosphere or from other portions of the environment to test for the presence of dangerous pollutants. A very immediate concern has been the need to test for the presence of informative or dangerous impurities in the human bloodstream, and anodic stripping voltammetry has proven itself capable of performing such tests. The present inventor and his associates have been interested in problems relating to this general field of activity for a number of years. Among other things, they have devised and developed certain useful apparatus for anodic stripping voltammetry as disclosed in application Ser. No. 167,330 (now abandoned) and certain improved electrodes disclosed in Ser. No. 168,161 (now abandoned) and Ser. No. 327,788, now U.S. Pat. No. 3,855,099, granted Dec. 17, 1974. The present invention is a unified system for anodic stripping voltammetry or cathodic stripping voltammetry capable of performing analysis of trace materials on an extremely rapid and an extremely accurate basis. In particular, the system according to the present invention can analyze human blood samples in the field or in the normal environment of such human beings at the rate of many hundreds of samples per day and can obtain critical output data regarding the presence of impurities such as lead, cadmium, zinc or the like in the human bloodstream within about a minute after a blood sample is actually taken from the human being, thus permitting such sampling in the environment of the real world. The quickness of completion of testing is of unusual importance, in light of experience which shows that the 7% of people tested in urban slum areas cannot later be located if they are once allowed to leave the test area.

GENERAL NATURE OF THE INVENTION

The present invention is a unified system, preferably automated, for electrochemical testing. In its usual embodiment it is an automated system for anodic stripping voltammetry. According to a preferred form of the invention, a sample holder is removably positioned to receive a special electrode having a very large, smooth active electrode surface. On the turn of a switch, electrical means are actuated to apply a cathodic potential to the electrode, plating out cations on the electrode, after which the electrical means apply the operating anodic voltage to strip out the deposited cations and monitor the potential and current.

The anodic stripping potential desirably is pulsed and the pulses changed in voltage in a stepwise mode. Each step desirably is raised 0.01 volts. The initial few pules on each step are ignored and the remainder are counted and measured. The readout is either charted or digitalized. The potential at which electrolytic current flows is an identification of the specific cations being stripped, and the quantity of current is a quantitative measure of the cation.

A presently preferred use and application of the invention is measurement of heavy metals such as lead in the human blood stream. A blood sample is taken, and an aqueous solution containing a metallic ion such as $Cr^{3+}$ or $Ca^{2+}$ is added to exchange with the lead complexed with the blood. The sample is then placed in operating position on the apparatus and the switch turned on. A lead content of 40 micrograms of lead per 100 ml of blood is a recognized standard of a dangerous level of lead in the human blood stream. In broader usage and application, identification and measurement of different metals in blood is now thought to have medical diagnostic value: for example, the profile of zinc and copper appear to be one diagnostic test for leukemia.

The apparatus according to the present invention can employ various kinds of waveforms to accomplish various different tests and to accommodate numerous electrical or chemical problems. The output may be in chart form, but one of the advantageous results is that there can be direct digital readout obtained essentially automatic and directly calibrated in end units; in practice, for example, the digital readout of lead in blood samples is directly in terms of micrograms of lead per 100 ml of blood. With calibrated digital readout, all the operator need do is record a single number.

The cell and electrode structure employs a hollow electrode with inner and/or outer surfaces active. Coaxial stirring produces reliable, reproducible results with an unusually fast time constant, and the preferred chemical ion exchange procedure joins with structure and method to give results on the spot. As presently in practical use, the system gives test results on biological samples within a minute or two, and it is well adapted to give equally fast results on other types of samples.

The system also has a high degree of flexibility to use conventionally prepared (digested) samples or non-digested samples, to use biological material such as blood or tissue or non biological samples such as paint, gasoline or other "environmental" materials for tests of lead or other metals, to use industrial materials for sampling and testing, and to test for a wide variety of metals including lead, cadmium, copper, zinc, thallium, silver, gold bismuth and the like.

The nature of the invention is further illustrated in the drawing in which.

DETAILED DESCRIPTION OF THE INVENTION

Figure 1:
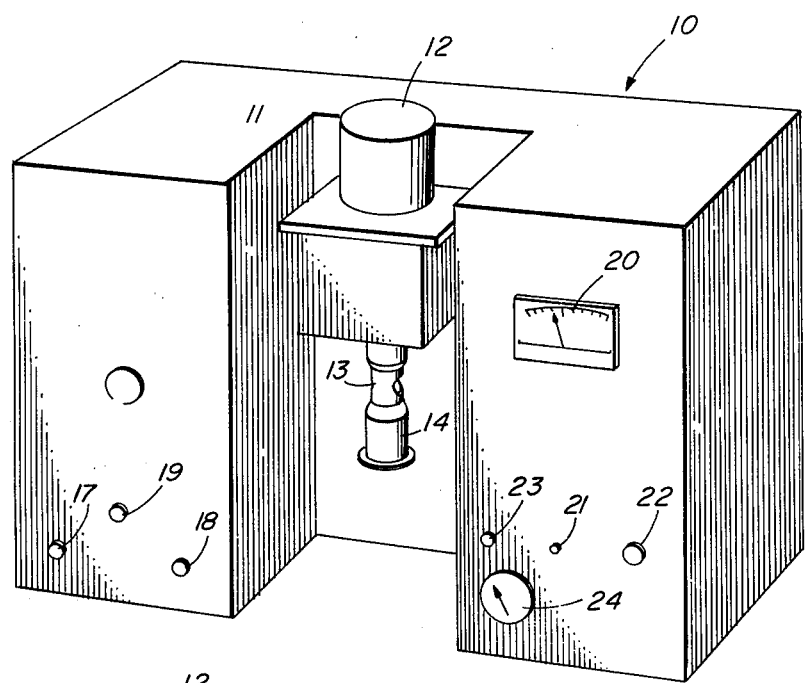
FIG. 1 is a perspective view of testing apparatus according to one embodiment of the invention.

In FIG. 1 is illustrated a cabinet generally designated 10 on which is mounted a support assembly 11 serving as a cell and motor support. Mounted on the support assembly 11 is a motor 12. Mounted beneath the support assembly 11 is an electrode 13 held in an electrode head 14. The electrode 13 is adapted to fit within a sample holder (not shown). The sample holder in practice is a plastic or glass member shape essentially like a test tube and characterized by being made of a material which is free from detectable quantities of any metal for which testing is to be performed. One principal intended use of the apparatus, according to this invention, is testing for trace quantities of lead and accordingly, the sample holder is made of lead-free glass or plastic which has been additionally treated to eliminate detectable trace quantities of lead. Desirably the support assembly 11 is pivotally mounted in the cabinet by means of mounting pins 16 whereby the entire assembly may be rotated in our out of position for easy insertion or removal of a sample holder from the head 14 on which it is held by a snug fit between the head and the sample holder.

On the cabinet is positioned in a convenient location, an off/on switch 17, an off/on motor switch 18, and desirably, a reset switch 19. Also, on the front of the cabinet is a meter 20 for visual read out of voltage or current recorder, off/on switch 21, a sweep offset 22, and a recorder offset button 23. Desirably, there is also on the cabinet face a current range indicator 24.

Figure 2:
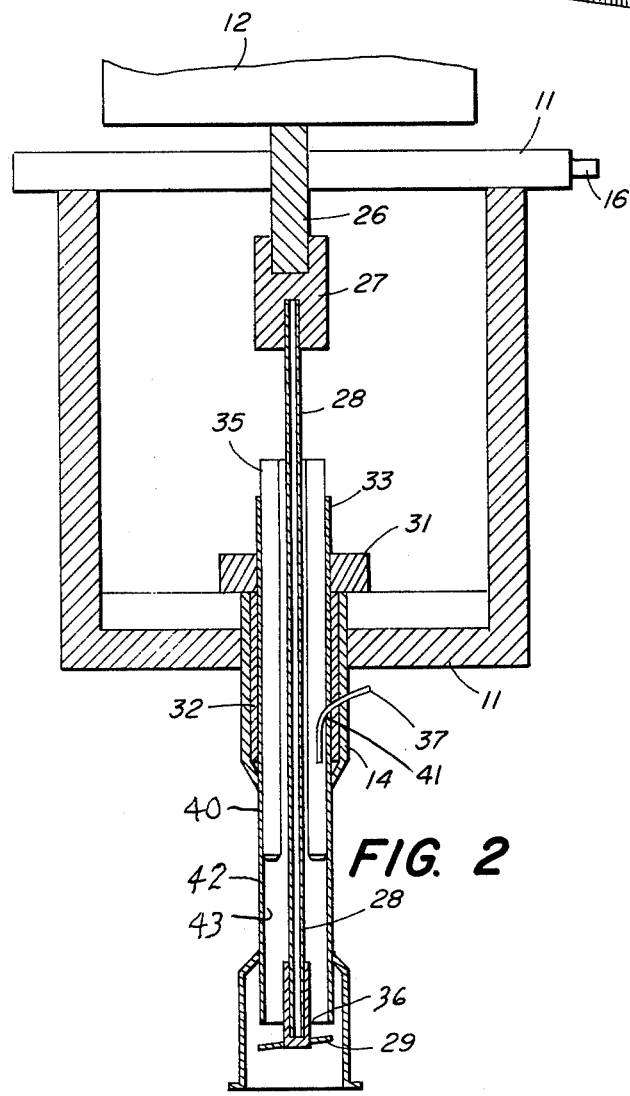
FIG. 2 is a front view, partially in section, of sample support apparatus according to the embodiment of FIG. 1.

In FIG. 2 is illustrated further detail of the cell and motor assembly. Mounted on support assembly 11 is motor 12 having a shaft 26 extending therefrom. By means of a coupling 27 the shaft 26 is connected to a propeller shaft 29 which terminates in a propeller blade 29 positioned within and near the bottom of electrode shield 14. Mounted at the bottom of support assembly 11 is an electrode holder 31 which is adapted and positioned to hold the electrode shield 14. Mounted within the electrode shield 14 is a stop 32 receiving and bearing against the electrode shield 14. The electrode 33 is in turn positioned within the stop 32 and is held in its proper position thereby. Mounted within the electrode are dividers 35 forming internal electrode compartments through which extends propeller shaft 28 and which, among other thing, serves as a guide for the propeller shaft. In practice three dividers are employed to form compartments. A bearing 36 at the bottom of the electrode compartment rotatably holds and guides the propeller. Optionally, a fine tube 37 or nitrogen line is positioned extending through the electrode shield and electrode with its nozzle positioned within the electrode compartment to assure a neutral atmosphere.

The electrode 33 is constructed and adapted for anodic stripping voltammetry or other electrode chemical operation. The electrode 33 consists of a hollow cylindrical electrode 40 desirably having one or more openings 41 in its side. The electrode body 40 according to one form of this invention is a hollow cylinder of graphite impregnated with a film forming material such as paraffin wax or the like and having on its surface a deposit of an electrode surface layer such as, for example, a layer of mercury. The electrode surface layer is present in the form of a multiplicity of dots or islands of mercury, each deposited on a graphite point and surrounded by a portion of impregnated wax surface. The electrode can be produced by impregnating a graphite rod with wax, scraping the wax from the graphite surface to lay bare a multiplicity of graphite points and coating mercury thereon by electrode chemical disposition using the graphite body as an electrode chemical cathode. The preparation of mercury coated graphite electrode described in co-pending application Ser. No. 168,161 referred to herein before.

In at least exposed active areas of the electrode area 33 according to one embodiment of the invention, both the outer surface 42 and the inner surface 43 of the electrode body 40 are coated with the electrode metal as described. When the apparatus of the present invention is employed for testing for trace elements of lead, the electrode metal preferably is mercury. In this manner a mercury electrode surface is positioned vertically within the sample holder and has an extremely high ratio of surface area in relation to sample volume. The area/volume relationship should be at least 3 cm$^2$ electrode area per milliliter sample volume, and preferably 4:1 or greater. At present, an electrode to sample ratio is 20 cm$^2$ per 3.6 milliliter sample. The propeller shaft 28 passes through the center of the electrode 33 and propeller blade 29 is positioned near the base of the electrode and is adapted to cause circulation of the sample liquid both inside and outside the electrode body 40.

Apparatus of the type herein disclosed can be employed by means of manual switching and manual controls in anodic stripping voltammetry. In such manual operation a sample holder containing a liquid for test is placed in position with the electrode assembly immersed therein. The electrode is connected in cathode mode to a suitable power source and ionic components are deposited on the electrode surface. In particular, if the apparatus is employed to test for the presence of lead, then lead is electrolytically deposited on the mercury electrode surface and is alloyed therein. After cathodic deposition on the electrode surface, the electrode is placed in anodic mode and the voltage applied thereto is gradually raised, and the electrolytic current is monitored. Metallic elements are identified by the potential or voltage of which the flow of current indicates that a trace of metal is being anodically stripped from the electrode and the quantity of the trace element is measured by the quantity of anodic current.

Figure 3:
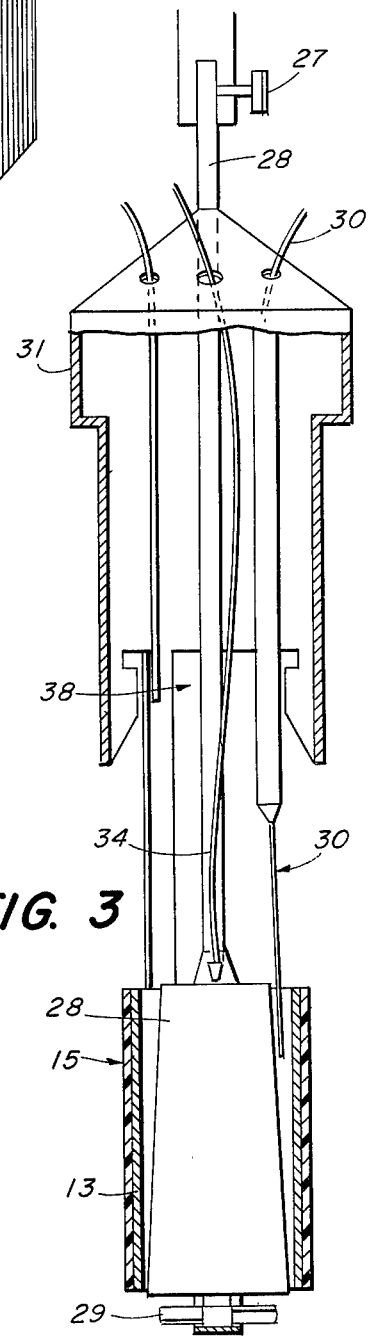
FIG. 3 is a front view, partially in section of electrode assembly components according to another embodiment of the invention.

In FIG. 3 is illustrated a modified electrode assembly in which the electrode 13 is mounted on a support or holder 31 and adapted to fit within a suitable sample holder (not shown) in much same manner as with the assembly in FIG. 2. A coupling 27 connects the motor 12 (see FIG. 1) with a propeller shaft 28 extending axially through holder 31 and to a point approximately level with the electrode 13. The electrode 13 is hollow, as with the electrode shown in FIG. 2, and within the hollow electrode the propeller shaft 28 is of significantly bigger radius leaving only a relatively small space between shaft 28 and inner surface of electrode 13. At the bottom of this shaft, once again, is a propeller blade 29. A counter electrode 30 extends through the electrode holder 31 and is positioned to be immersed in the sample within the sample holder. A reference electrode 34 also extends through the holder 31 to a position within the sample. Desirably, the counter electrode 30 is a platinum wire which may directly contact the solution or, as presently preferred, is a platinum electrode contained in a porous glass compartment or shell. The reference electrode desirably is a silver or silver chloride wire immersed in a saturated sodium chloride solution. Desirably the propeller shaft 28 may extend through one or several bearings (not shown). In the preferred form of the structure, the electrode holder 31 is adapted to fit snuggly within a sample holder so that during operation a sample holder is retained firmly but releasably in a position into which it can be manually fitted.

In one form of the invention, as illustrated in FIG. 3, the electrode 13 has a coating 15 on its outer or exposed surface. This coating is a plastic tubing shrunk around the outside of the active electrode. When the coating is employed, the electrode is generally protected from accidental damage and can, in fact, be handled carefully when the electrode is removed from a sample. There is relatively small clearance between the electrode and the sample holder when in position, and again is there relatively small clearance between the electrode and the lower end of stirrer 28. Moreover, the stirrer 28 is slightly tapered, being slightly larger at its lower end than it is at the upper end, so that the space between this stirrer 28 and the inner electrode surface also is tapered, being narrower at the bottom than at the top. As the stirrer rotates within the electrode, this tapering causes not only localized currents of the test liquid, but also causes a general flow of the liquid downwards in the space between stirrer and electrode.

In high speed sample testing it is important that the sample liquid should circulate well, but it is also desired that the relatively still layer adjacent to the electrode be as thin as practical. This layer, known as the Nernst layer, appears to be about 1-2 micron in the apparatus of FIG. 3.

Figure 4:
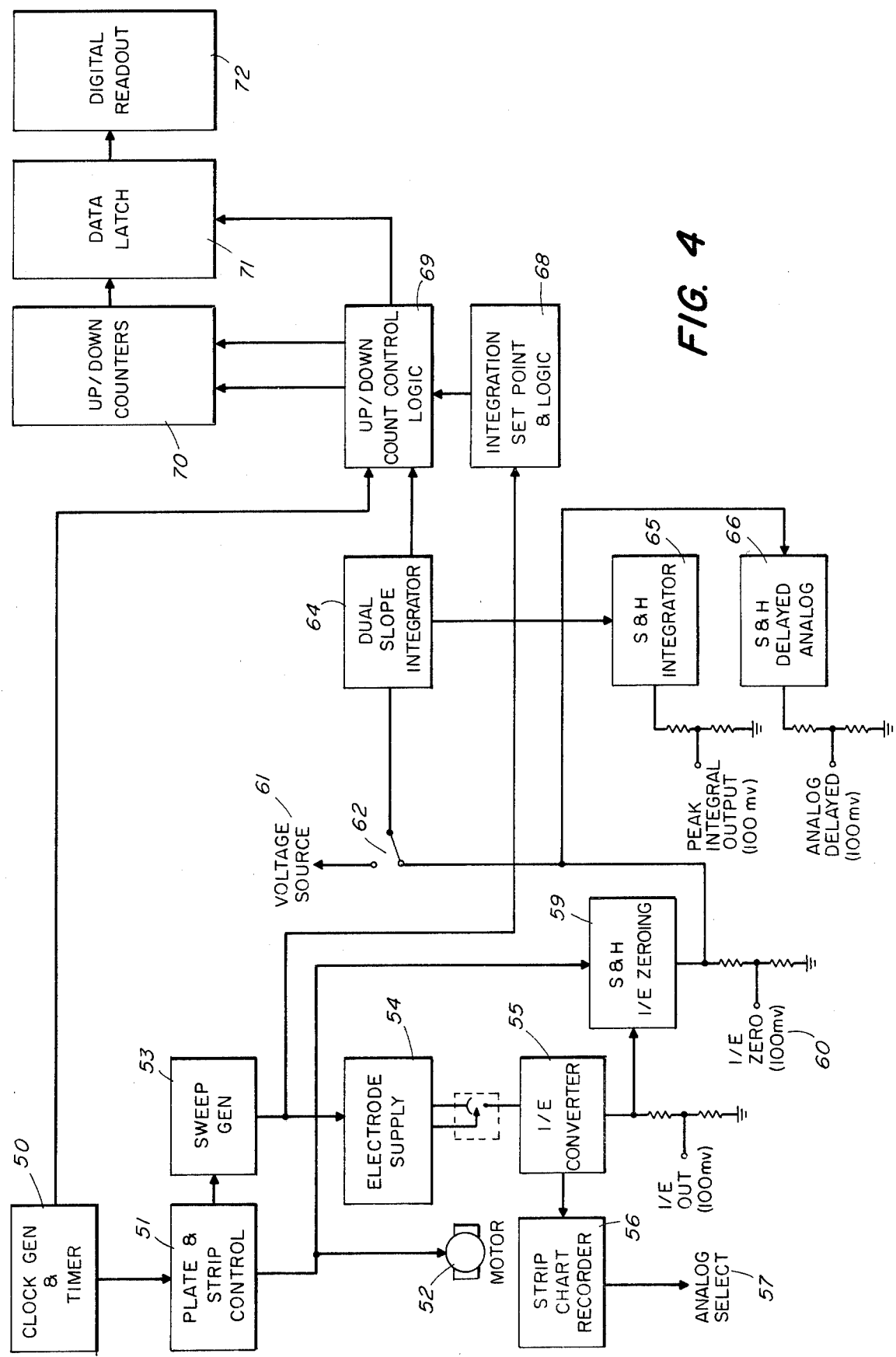
FIG. 4 is a block diagram of an electrical system in conjunction with apparatus according to one embodiment of the invention.

In FIG. 4 is illustrated, in the form a block diagram, the electrical controls for automation of the equipment according to one embodiment of the invention. A clock generator and timer controlled sequence serves as a control mechanism for all functions. A plate and strip control 51 serves to apply a plating potential to the electrode and under the control of the timer 50 applies such control for a period of one minute or selectively for some other period of time such as 3 minutes or 5 minutes. A motor 52 energizes the stirring mechanism (propeller shaft 28 and 29) and under the control of timer 50, causes stirring of the sample while the plating potential is applied.

A sweep generator 53 is adapted to supply a stripping voltage to electrode 32 and under the control of timer 50, supplies this voltage 10 seconds after the plate and strip control 51 and motor 52 and turned off by the timer 50. The sweep generator 53 is essentially a staircase generator and steps down in 10 millivolt steps at 100 milliseconds per step. When the apparatus is used for detection and measurement of lead, the plating voltage is −1.0 volts and the sweep generator steps down from −1.0 volts to 0.1 volts in 90 steps in an elapsed time of about nine seconds. The sweep generator operates through an electrode supply 54.

Adapted to read out from the electrode during stripping, and optionally during plating, is an I/E converter which serves to convert current to voltage to supply a signal more suitable for being amplified. The I/E converter 55 feeds to an optional strip chart recorder 56. As will be seen hereinafter, the apparatus under the control of the elements in FIG. 4 produces a direct digital readout but a chart readout may be desired and is illustrated in FIG. 4. This readout, when employed, is a conventional charting device to chart current flow vs. time; the current flow being expressed in terms of voltage output from the I/E converter 55. The time vector, is related to the output of sweep generator 53, identified and stripping voltage. The chart represents, therefore, the readout from the electrode and is shown in the figure as an analog selector 57.

An S & H I/E zeroing unit 59 (sample and hold) delays for a selected time which, in operation, may be 20 milliseconds, before counting the electrode output. In order to eliminate initial noise upon each change in step as the stripping potential is stepped down, an I/E zero selector 60 is set for a zero point at 100±50 millivolts before the integration zone.

A connection to a power supply or voltage source 61 operates through switch 62 energize the various electrical components, energizes the timer 50 and the other power units previously and hereinafter described. For digital readout, which is a presently preferred embodiment of the invention, a dual slope integrator 64 integrates the output signal and converts the analog signal to a digital representation. An S & H integrator 65 operates from the dual slope integrator 64 to identify and isolate the zone of the stripping potential in which the current signal occurs. An S & H delayed analog 66 optionally permits a variation in sample and hold time. This adjustability is not required if the apparatus is employed for a single use and the application, as is now the case where the apparatus is employed for the detection of lead which has a single deplating or stripping potential.

An integration set point and logic circuit 68 is adapted to receive the readout signal and to discard as noise an initial signal less than a pre-determined value. This integration setpoint and logic 68 then, together with an output from the dual slope integrator 64, feeds to an up/down count control logic 69. This up/down count control logic 69, for its first count, counts down six times and next, for twelve counts, counts up followed by a fourteenth count which, once again, counts down six times thus making a count equivalent to a digital output from the output signal. The up/down count control logic 69 in turn feeds to an up/down counter 70 and to a data latch 71 which finally feeds to a digital readout 72. The up/down counter 70 merely counts the signal received from the up/down counter control logic 69 in the number and direction designated by such logic. The data latch 71 brings the process to a halt after the signal in the desired zone has been completed. The digital signal received from the total count from up/down counter 70 and is converted into a digital reading thus corresponding to a digital representation of quantity of metal or other ion detection and measurement. In practice, this readout is set to present digitally a direct reading of micrograms of lead per 100 cc of blood sample. The digital readout 72 can, accordingly, be set to translate a signal to correspond to any desired digital measure.

Figure 5:
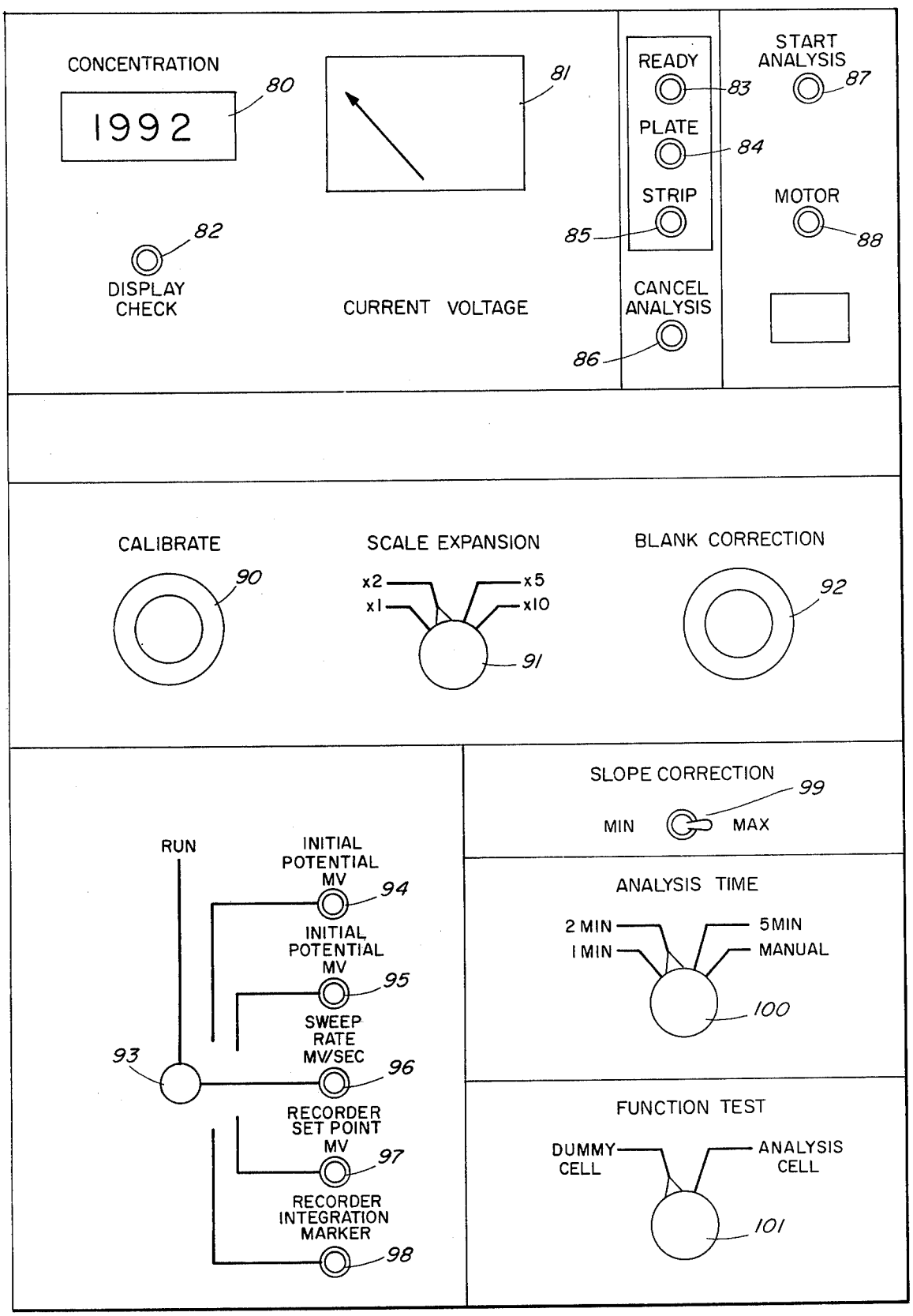
FIG. 5 is a front view of a front control panel of apparatus according to a modified embodiment of the invention.

In FIG. 5 is shown the panel of apparatus which may operate in accordance with the diagram of FIG. 4. The upper part of the panel is normally visible; the lower portion may be covered after the appropriate settings and calibration are made.

A digital display 80 reads out and displays the digital record of a test while a meter 81 may indicate the current flow or voltage during a run. An indicator lamp panel has lights for "ready" 83, "plate" 84 and "strip" 85 indicating the phase of the operation. A push button 86 labelled "cancel analysis" operates to interupt and return the analysis to zero. At the upper right hand corner a push button 87 labelled "start analysis" is adopted to start timer 50, and pushing this button is the only act required of the operator once the sample is in place. A motor light 88 indicates when motor 52 is operating.

Adapted for preliminary set up and calibration is a lower panel. A potentiometer 90 is adjustable, being adapted to control the digital readout 72 of FIG. 4, desirably so that the readout is directly in the correct digital units. When blood is tested for lead, this readout is set against a known standard sample so that the readout is the number of micrograms of lead per 100 milliliters of blood. A rotary switch 91 selects a desired scale expansion if needed, and a blank correction potentiometer 92 is adjustable to set a desired zero point.

In the lower left corner of the panel is a run indicator 93, with screw potentiometers 94, 95, 96, 97 and 98 for indicated settings for initial potential, sweep rate, recorder set point and recorder integration. Finally, in the lower right is a slope correction setting 99, a rotary switch 100 selecting one of several automatic time controls for timer 50 (or selecting a manual control) and a "function test" switch 101 for selecting a dummy cell or analysis cell for calibration or other purposes.

The panel of FIG. 5 serves the purpose that in part illustrates the instrument and in part illustrates the ease of operation. A skilled operator can first set and calibrate the instrument for a specific test condition, after which an operator who may be unskilled measures a predetermined quantity of sample into a prepackaged sample holder, places the sample holder on the machine, pushes the "start analysis" button 87 and a minute later reads the result in digital display 80.

The apparatus discussed, herein in accordance with the present invention is intended to be employed for detection and measurement of trace quantities of certain heavy metals including zinc, cadmium, lead, copper, busmuth, silver, gold and thallium. Analysis can be made of nanogram quantities of these trace metals in periods of time of a few seconds up to one or occasionally several minutes. In particular, it is possible to detect and measure quantities of certain of these trace elements in the human blood stream. One of the very important social purposes of this invention is the detection and measurement of small quantities of lead in the human blood stream and in particular, in the blood stream of children residing in city slum areas.

For such lead detection and measurement, the desired sample holder is a test tube shaped plastic or glass vessel made of lead-free glass or lead-free plastic. Desirably, the sample holder is preconditioned by electro-chemical treatment to electrolyze out of the glass any trace quantities of lead which may originally have been present. A reagent solution is prepared in advance containing a dissolved chromium or calcium ionic material $Cr^{+3}$ or $Ca^{+2}$. A measured sample of blood is taken from a human blood stream. A small quantity of the chromium or calcium reagent is added, and as presently preferred, a mixed calcium-chromium reagent is employed. The precise amounts and concentrations can be adjusted for convenience, provided a standard procedure is adopted and suitable calibration made. It has been found satisfactory to employ $CrCl_3$ prepared with 0.03 to 0.04 molar $Cr^{+3}$ in 0.001 to 0.02 molar HCl; this chromium ion solution may be employed in the amount of 3.6 cc to exchange the lead in 100 microliters of blood sample. At present, there is used a dilute solution of calcium chloride, chromium trichloride, hydrogen ion, perchlorate ion and a dispersing agent (Surfynol 104 is the agent currently employed, and is believed to be a non-ionic higher alcohol wetting agent). The reagent components now used in laboratory standardized tests are:

$CaCl_2$: 0.08F
$CrCl_3$: 0.04F
$HgCl_2$: 0.000225F
$H_2NNH_2-(HCl)_2$: 0.019F
Surfynol104: 0.001 weight percent
$ClO_4$: 0.0458F
$H^+$: 0.0398 (to bring to pH 1.4)

The mixture of calcium ion and/or chromium ion cause release of complexed lead in the blood so that the total concentration of lead in blood can be effectively measured when one of the reagents just described is employed in the equipment and method of the invention.

Heavy metals which are complexed or bound in other sample materials can also be released. For example, a mix of 0.01 molar bromide ion; 0.1 molar NaCl; 0.01 molar $HNO_3$; and 0.01% Triton X-100 (a polyalcohol) is suitable for releasing lead in gasoline. The same and other releasing components can be used to release the various heavy metals from a wide variety of organic samples. What is used is a metal ion or mixture of metal ions which will displace the test metal and which will not plate out or strip out at the plating or stripping potentials used in detection and measurement of the metal being tested.

After the test material is treated with a release agent, or after other sample preparation as may be necessary such as digestion, or other treatment and dilution or concentration as needed, the sample in the sample holder is placed in position on the apparatus and the apparatus is turned on. The chromic ion in the solution acts to displace lead from any complexes which it may have formed with components of the blood sample, and the chromium does not plate out at the operating potentials used for lead analysis. Within a sixty second operating time, the apparatus will cause any lead to be largely deposited on or in the mercury electrode coating and thereafter anodically stripped from the electrode with both identification and quantitative measurement. An important value of the invention is that the detection and measurement can be carried out in a time of no more than a minute or two after extraction of the blood sample from the blood stream so that the person himself can be advised as to the test results without being required to return on a subsequent occasion or even being required to wait for a significant period of time for such test results.

A presently preferred sample holder is a self-contained unit which is factory preconditioned. It comprises a plastic sample holder cylindrical in shape having a volume of 5 cc. and containing 3.6 millimeters of a liquid sample which contains chromic ion, mercury, hydrogen and hydrocloric acid. It is sterilized, purified to remove lead, or to remove other metallic ion being tested and measured and sealed.

I claim:

1. An electrode assembly for stripping voltammetry analysis of a sample solution, and comprising in combination:
   an enclosure for holding a volume of said sample solution,
   a counter electrode located in said enclosure for contacting said sample solution;
   a working electrode located in said enclosure for contacting said sample solution, said working electrode being in the form of an axially hollow electrode body having a metal active electrode surface formed on the interior surface thereof;
   and rotatable stirring means (i) extending into the hollow of said electrode body, closely spaced (a) from the interior surface of said hollow and (b) from said counter electrode, and (ii) adapted to produce flow of said sample solution across said active electrode surface, said electrode assembly being dimensioned so that the ratio of surface area of said active electrode surface to sample volume is at least 3 cm$^2$/ml.

2. An electrode combination according to claim 1, wherein said working electrode comprises a hollow graphite body.

3. An electrode combination according to claim 2, wherein said hollow graphite body has an active electrode surface in the form of a multiplicity of islands of mercury formed on the interior surface of said hollow graphite body.

4. An electrode combination according to claim 3 wherein said hollow electrode body comprises a wax impregnated hollow graphite cylinder, and said islands of mercury are deposited on graphite points surrounded by a portion of said wax.

5. An electrode combination according to claim 3 wherein said active electrode surface is also formed on the exterior surface of said hollow graphite body.

6. In Apparatus for use in electrochemically testing a sample solution by stripping voltammetry, in which ions present in a volume of said sample are first deposited on a working electrode in contact with said sample solution by applying a first potential on said working electrode, and thereafter the potential on said working electrode is varied so as to strip the deposited ions from said working electrode back into solution, and including an enclosure for holding a quantity of said solution for testing, the improvement wherein (A) said working electrode comprises an axially hollow cylindrical body (i) formed of an electrically insulating material and (ii) having an active electrode surface covering the interior surface of said hollow body at least in part, (B) rotatable stirring means extending into the hollow of said electrode body and closely spaced from said electrode active surface; and (C) the ratio of surface area of said active electrode surface to sample volume is at least 3 cm$^2$/ml.

7. In apparatus according to claim 6, wherein said ratio is at least 4 cm$^2$/ml.

8. In Apparatus according to claim 6, wherein said active electrode surface also covers the exterior surface of said hollow body at least in part.

9. In apparatus according to claim 6, wherein said rotatable stirring means is adapted to cause localized currents of said sample solution to flow across said active electrode surface.

10. In apparatus according to claim 6, wherein said hollow electrode body is dimensioned to fit snuggly within said enclosure.

11. In apparatus according to claim 6, wherein said rotatable stirring means comprises a propeller blade mounted on one end of a rotatably driven propeller shaft, and said propeller shaft is slightly tapered, being slightly larger at its lower end than it is at its upper end, whereby rotation of said propeller shaft and propeller produces a general flow of said sample solution downwards in the space between said stirrer and said active electrode surface.

12. In apparatus according to claim 6, and further including a counter electrode having an active electrode surface located in contact with said solution, a reference electrode having an active electrode surface located in contact with said solution, and means connecting (a) said counter electrode to a working potential, (b) said reference electrode to a reference potential, and (c) said working electrode to a working potential.

13. In apparatus according to claim 12 and further including a variable power supply and timer control adapted to first apply a positive potential to said working electrode for a period of time, and then to sweep down the potential on said working electrode over a period of time.

14. Apparatus according to claim 12 including:
   means to apply a first potential of a first polarity to said working electrode to cause deposition thereon of material corresponding to said ions being tested,
   means to pulse a staircase potential of opposite polarity to said working electrode to strip from said working electrode the ions deposited thereon by said first potential, said staircase potential spanning the stripping potential of said ions,
   means to measure and integrate the current flowing to said working electrode in said staircase potential, and
   means to display information corresponding to the integrated current flow.

15. Apparatus according to claim 14, wherein said working electrode active surface comprises a metal surface formed on the interior surface of said electrode hollow body, said active surface being electrically connected through said hollow body to said means to apply said first and said staircase potential to said electrode.

16. The apparatus of claim 15, wherein said electrode body comprises a hollow graphite body.

17. The apparatus of claim 16, wherein said active electrode surface comprises a multiplicity of islands of mercury formed on the interior surface of said hollow body.

18. In apparatus according to claim 12, and further including a variable power supply and timer control adapted to first apply a negative potential to said working electrode for a period of time, and then to sweep down the potential on said working electrode over a period of time.

* * * * *